(12) United States Patent
Pham et al.

(10) Patent No.: US 12,315,631 B2
(45) Date of Patent: May 27, 2025

(54) MEDICAL DEVICE SITE MONITORING METHODS AND RELATED DEVICES AND SYSTEMS

(71) Applicant: MEDTRONIC MINIMED, INC., Northridge, CA (US)

(72) Inventors: An Thien Pham, Rosemead, CA (US); Megan V. Becvarik, Los Angeles, CA (US); Emilian S. Istoc, Canoga Park, CA (US); Sean M. Milar, Northridge, CA (US); Sophia Wolf, Pasadena, CA (US); Xinrui Zhang, Yorba Linda, CA (US); Evan Anselmo, Northridge, CA (US); Yevgeniy Levin, West Hills, CA (US); Sarnath Chattaraj, Simi Valley, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 853 days.

(21) Appl. No.: 17/086,147

(22) Filed: Oct. 30, 2020

(65) Prior Publication Data
US 2021/0142902 A1    May 13, 2021

Related U.S. Application Data

(60) Provisional application No. 62/932,453, filed on Nov. 7, 2019.

(51) Int. Cl.
*G16H 50/20* (2018.01)
*G06F 3/0482* (2013.01)
(Continued)

(52) U.S. Cl.
CPC ........... *G16H 50/20* (2018.01); *G06F 3/0482* (2013.01); *G06T 11/00* (2013.01); *G16H 10/60* (2018.01);
(Continued)

(58) Field of Classification Search
CPC ........ G16H 50/20; G16H 10/60; G16H 15/00; G16H 20/00; G16H 20/17; G16H 40/20;
(Continued)

(56) References Cited

U.S. PATENT DOCUMENTS 4,562,751 A    1/1986 Nason et al.
4,685,903 A    8/1987 Cable et al.
(Continued)

FOREIGN PATENT DOCUMENTS

WO    2012170000 A1    12/2012
WO    2013033025 A1    3/2013

OTHER PUBLICATIONS

Nihat Baysal, et al: "Detectng Sensor and Insulin Infusion Set Anomalies in an Artificial Pancreas", 2013 American Control Conference (ACC), IEEE, Jun. 17, 2013 (Jun. 17, 2013), pp. 2929-2933, XP032476248, ISSN: 0743-1619, DOI: 10.1109/ACC.2013.6580279.

(Continued)

*Primary Examiner* — David J Stoltenberg
*Assistant Examiner* — Tran N Nguyen
(74) *Attorney, Agent, or Firm* — Weaver Austin Villeneuve & Sampson LLP

(57) ABSTRACT

Patient monitoring systems and related medical devices and methods are provided. One method involves obtaining historical usage data associated with a patient for a plurality of potential site locations for a medical device, classifying one or more site locations of the plurality of potential site locations into a viable group of potential site locations for the patient based at least in part on the historical usage data, and providing, at a client device, graphical indicia of the one or more site locations classified into the viable group of potential site locations.

19 Claims, 9 Drawing Sheets

(51) Int. Cl.

| | | |
|---|---|---|
| *G06T 11/00* | (2006.01) | |
| *G16H 10/60* | (2018.01) | |
| *G16H 15/00* | (2018.01) | |
| *G16H 20/00* | (2018.01) | |
| *G16H 20/17* | (2018.01) | |
| *G16H 40/20* | (2018.01) | |
| *G16H 40/67* | (2018.01) | |
| *G16H 50/30* | (2018.01) | |
| *G16H 50/50* | (2018.01) | |
| *G16H 50/70* | (2018.01) | |
| *A61B 5/145* | (2006.01) | |
| *A61M 5/142* | (2006.01) | |
| *A61M 5/172* | (2006.01) | |

(52) U.S. Cl.
CPC ........... *G16H 15/00* (2018.01); *G16H 20/00* (2018.01); *G16H 20/17* (2018.01); *G16H 40/20* (2018.01); *G16H 40/67* (2018.01); *G16H 50/30* (2018.01); *G16H 50/50* (2018.01); *G16H 50/70* (2018.01); *A61B 5/14532* (2013.01); *A61M 5/14244* (2013.01); *A61M 5/1723* (2013.01); *G06T 2210/41* (2013.01)

(58) Field of Classification Search
CPC ........ G16H 40/67; G16H 50/30; G16H 50/50; G16H 50/70; G16H 40/40; G16H 40/63; G06F 3/0482; G06F 3/04842; G06T 11/00; G06T 2210/41; A61B 5/14532; A61B 5/4839; A61M 5/14244; A61M 5/1723; A61M 2205/3561; A61M 2205/3584; A61M 2205/502; A61M 2205/52; A61M 2205/583; A61M 2205/8206
USPC ........................................................ 705/2–3
See application file for complete search history.

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |
| 10,201,657 B2 | 2/2019 | Parikh et al. |
| 10,272,201 B2 | 4/2019 | Loutseiko et al. |
| 2006/0031094 A1 | 2/2006 | Cohen et al. |
| 2007/0123819 A1 | 5/2007 | Mernoe et al. |
| 2007/0187476 A1* | 8/2007 | Durrell .................. G16H 10/60 235/375 |
| 2010/0160861 A1 | 6/2010 | Causey, III et al. |
| 2011/0144479 A1* | 6/2011 | Hastings .............. A61B 5/6861 600/424 |
| 2013/0245461 A1* | 9/2013 | Maier-Hein ......... A61B 90/361 600/476 |

(56) References Cited

U.S. PATENT DOCUMENTS

| | | | |
|---|---|---|---|
| 2013/0338630 | A1 | 12/2013 | Agrawal et al. |
| 2014/0066889 | A1 | 3/2014 | Grosman et al. |
| 2015/0057634 | A1 | 2/2015 | Mastrototaro et al. |
| 2015/0057807 | A1 | 2/2015 | Mastrototaro et al. |
| 2016/0191887 | A1* | 6/2016 | Casas .................. H04N 13/156 348/47 |
| 2017/0049962 | A1 | 2/2017 | Parikh et al. |
| 2017/0049964 | A1* | 2/2017 | Varsavsky ............. G16H 40/40 |
| 2019/0201622 | A1* | 7/2019 | Loutseiko ............. G16H 40/63 |
| 2019/0216452 | A1* | 7/2019 | Nawana ............... A61B 5/0022 |
| 2020/0009321 | A1* | 1/2020 | Du ........................ G16H 40/63 |
| 2021/0038812 | A1* | 2/2021 | Loutseiko ......... A61M 5/14244 |
| 2021/0407645 | A1* | 12/2021 | Bazargan ............... G16H 20/17 |

OTHER PUBLICATIONS

Marzia Cescon, et al: "Early Detection of Infusion Set Failure During Insulin Pump Therapy in Type 1 Diabetes", Journal of Diabetes Science and Technology, vol. 10, No. 6, Sep. 12, 2016 (Sep. 12, 2016), pp. 1268-1276, XP055442304, US ISSN: 1932-2968, DOI: 10.1177/1932296816663962.

D. Barry Keenan, Ph.D., et al., Delays in Minimally Invasive Continuous Minotoring Devices: A Review of Current Technology, Journal of Diabetes Science and Technology, vol. 3, Issue 5, Sep. 2009, pp. 1207-1214, Diabetes Technology Society.

Desmond Barry Keenan, Ph.D., et al., Accuracy of the Enlite 6-Day Glucose Sensor with Guardian and Veo Calibration Algorithms, Diabetes Technology & Therapeutics, vol. 14, No. 3, 2012, pp. 1-7, Mary Ann Liebert, Inc.

Kerstin Rebrin, et al., Can Interstitial Glucose Assessment Replace Blood Glucose Measurements? Diabetes Technology & Therapeutics, vol. 2, No. 3, 2000, pp. 461-472.

Michael S. Boyne, et al., Timing Of Changes In Interstitial And Venous Blood Glucose Measured With A Continuous Subcutaneous Glucose Sensor, Diabetes, 2003, vol. 52, pp. 2790-2794.

Howard Wolpert, Establishing A Continuous Glucose Monitoring Program, Journal of Diabetes Science and Technology, vol. 2, Mar. 2008, pp. 307-310.

Howard Wolpert, Use Of Continuous Glucose Monitoring In The Detection And Prevention Of Hypoglycemia, Journal of Diabetes Science and Technology, vol. 1, Issue 1, Jan. 2007, pp. 146-150.

Sara Wilson Reece, Insulin Pump Class: Back To The Basics Of Pump Therapy, Diabetes Spectrum, vol. 27, No. 2, 2014, pp. 135-140.

Gary Scheiner, et al, Insulin Pump Therapy: Guidelines for Succesful Outcomes, American Association of Diabetes Educators 2008, Consensus Summit, Sep. 18, 2008, Chicago, IL.

* cited by examiner

MEDICAL DEVICE SITE MONITORING METHODS AND RELATED DEVICES AND SYSTEMS

CROSS-REFERENCE TO RELATED APPLICATIONS

This application claims the benefit of U.S. Provisional Patent Application Ser. No. 62/932,453, filed Nov. 7, 2019, the entire content of which is incorporated by reference herein.

TECHNICAL FIELD

Embodiments of the subject matter described herein relate generally to medical devices, and more particularly, embodiments of the subject matter relate to monitoring insertion site conditions associated with operation of a medical device.

BACKGROUND

Insertable medical devices are used for monitoring or managing the physiological condition of a user or patient. For example, infusion pump devices and systems are relatively well known in the medical arts, for use in delivering or dispensing an agent, such as insulin or another prescribed medication, to a patient. As another example, continuous glucose monitoring (CGM) sensors may be utilized to measure the glucose in the interstitial fluid (ISF) for improved monitoring of a patient's glycemic condition.

In practice, it is advisable for the insertable element (e.g., a cannula, needle, or the like) utilized with an insertable medical device to be changed or replaced periodically to prevent infection. Additionally, it is also advisable to periodically change or vary the location where the insertable element is inserted into the body, also known as the insertion site, in order to mitigate tissue resistance and maintain effectiveness of the insertion site. Failure to timely change the insertion site can have undesirable physiological consequences, such as a potential glucose excursion event. Accordingly, patients using infusion pump therapy have typically been instructed to replace infusion sets within a fixed period of time (e.g., every 2 to 3 days) that attempts to ensure preemptive replacement that provides a safety margin in advance of the time of when a particular infusion set at a particular insertion site is likely to lose effectiveness. While preemptively replacing an infusion set can be beneficial for safety purposes, it may also result in some infusion sets being replaced prematurely when it could otherwise be desirable to maximize the lifetime of the infusion set. For example, patients who are traveling, have a limited supply of infusion sets on hand, do not have immediate access to an infusion set, or experiencing other extenuating circumstances may prefer to avoid having to replace an infusion set according to a fixed schedule.

Additionally, some patients may forget to replace or rotate their infusion set. While providing reminders based on a fixed period of time may be effective, some patients may disregard or ignore the messages based on a perception that the infusion set is still functioning normally. Accordingly, there is a need to prolong the usable lifetime of an infusion set or other insertable element for a given insertion site currently in use while also ensuring that patients utilize potential insertion sites in a manner that mitigates potential adverse events.

BRIEF SUMMARY

Patient monitoring systems and related medical devices and methods are provided. An embodiment of a method involves obtaining historical usage data associated with a patient for a plurality of potential site locations for a medical device, classifying one or more site locations of the plurality of potential site locations into a viable group of potential site locations for the patient based at least in part on the historical usage data, and providing, at a client device, graphical indicia of the one or more site locations classified into the viable group of potential site locations.

In another embodiment, an apparatus for a computer-readable medium is provided. The computer-readable medium has computer-executable instructions stored thereon that, when executed by a processor, cause the processor to provide a first graphical user interface (GUI) display including a GUI element for receiving input of a device type for a medical device and identify a plurality of potential site locations for the medical device based on the device type in response to receiving indication of the device type. For each potential site location of the plurality of potential site locations, the instructions cause the processor to obtain a model for calculating a metric for the respective site location based on historical data for the respective site location, calculate a current value for the metric for the respective site location based at least in part on a current patient state using the model, and classify the respective site location into a respective one of a plurality of viability categories based on the current value for the metric, resulting in classifications of the plurality of potential site locations. The instructions further cause the processor to provide a second GUI display including graphical indicia of the classifications of the plurality of potential site locations overlying a graphical representation of a body of a patient.

In another embodiment, a system is provided that includes a database to maintain historical operational data and historical usage data associated with a patient for a type of medical device, a remote device coupled to the database, and a client device. The remote device is configured to determine, for each site location on a body of the patient of a plurality of potential site locations for the type of medical device, a model for calculating a metric indicative of health or performance of the respective site location based on a relationship between a respective subset of the historical operational data and a respective subset of the historical usage data associated with the respective site location. The client device is configured to provide a first graphical user interface (GUI) display including a GUI element for receiving user input indicative of a device type to be utilized and provide a second GUI display including graphical indicia of one or more site locations of the plurality of potential site locations classified into a viable category based on a respective current value for the metric for the respective site location, wherein the respective current value for the metric for the respective site location is determined based at least in part on a current patient state using the model for the respective site location.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
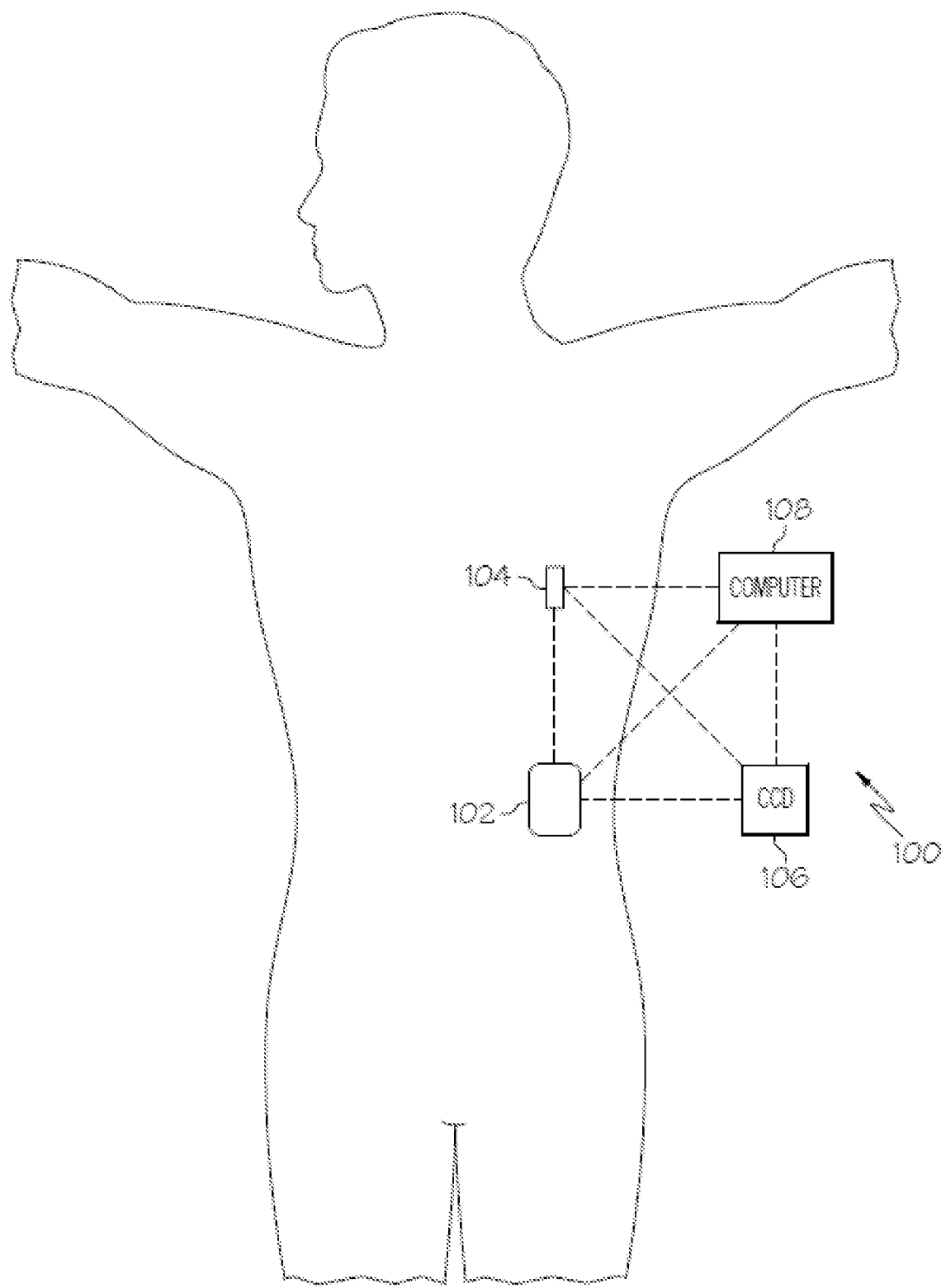
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device, exemplary embodiments described below are implemented in the form of medical devices, such as portable electronic medical devices. Although many different applications are possible, the following description focuses on embodiments that incorporate a fluid infusion device (or infusion pump) as part of an infusion system deployment. That said, the subject matter described herein is not limited to infusion devices (or any particular configuration or realization thereof) and may be implemented in an equivalent manner in the context of other medical devices, such as continuous glucose monitors (CGM) or other sensing devices, injection pens (e.g., smart injection pens), and the like.

For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos.: 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

In some embodiments, the subject matter described herein is implemented in the context of an infusion system including a fluid infusion device having a motor or other actuation arrangement that is operable to linearly displace a plunger (or stopper) of a reservoir provided within the fluid infusion device to deliver a dosage of fluid, such as insulin, to the body of a patient (or user). Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be autonomously generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

As described in greater detail below in the context of FIGS. 4-9, exemplary embodiments of the subject matter described herein facilitate rotation of insertion sites to allow tissues to heal, prevent lipohypertrophy, lipoatrophy, or other lipodystrophy, and reduce the likelihood of insertion site loss. In this regard, while many diabetic patients acknowledge the need to rotate insertion sites, many patients fail to do so due to the user burden, poor habits, or lack of information. Accordingly, the subject matter described herein eases user burden and enhances user experience, encourages site rotation, and improves therapy outcomes. The subject matter described herein may be implemented in connection with an infusion device or other infusion set, continuous glucose monitoring (CGM) or other sensor sites, or other injection regimens (e.g., multiple dose injection or multiple daily injection therapy).

Exemplary embodiments of the subject matter described herein employ an electronic device with communications capabilities, alternatively referred to herein as a site tracker, tracker, or variants thereof, such that is capable of communicating with another electronic device, such as, for example, a cellular phone, smartphone, or other client mobile device using wireless communications (e.g., Bluetooth or the like). In various embodiments, the tracker device could be integrated with, include or otherwise be realized as a portable insertable medical device, such as an infusion device, a sensing device, a CGM device, or the like. A software application, which may alternatively be referred to herein as a tracker algorithm) resides on the other device (e.g., a client device, a remote device or other cloud computing device, and/or the like) and is capable of supporting communications with the tracker device and/or other networked devices (e.g., a remote server, a remote database system, and/or the like) to support the subject matter described herein.

In exemplary embodiments, the application is capable of tracking the usage of various insertion sites and the extent to which the sites have experienced trauma, which may be calculated or otherwise determined based on the amount, duration, or frequency of usage of a respective insertion site. This includes but is not limited to any sort of infusion site, daily injection site, sensor usage site, the breaking of the skin at an insertion site via a needle or the use of an insertion site to deliver drugs my means of a cannula that remains in place for a time period. It should also be appreciated that the subject matter is not limited to insertion sites or insertable devices, and can be implemented in the context of site locations for transdermal devices or other medical devices, for example, to rotate site locations for a transdermal device to limit hardening of the subcutaneous layer (e.g., lipohypertrophy) in the area where the transdermal device is to be placed.

As described below, in exemplary embodiments, the tracker algorithm may utilize machine learning or other artificial intelligence techniques to learn or otherwise determine the potential insertion sites for a particular patient that are more likely to achieve a desired level of performance and/or the potential insertion sites that are more at risk for tissue trauma or site loss and provide corresponding guidance to the patient. In some embodiments, the tracker application provides or otherwise communicates with a remote device or another cloud-based platform that supports predictive monitoring of infusion site rotation and health based on collected insertion site usage data. In this regard, information input by a patient pertaining to a particular insertion site or the subjective performance thereof may be collected and utilized in conjunction with the patient's insulin delivery data, sensor glucose measurement data, blood glucose measurement data, and/or the like. Based on correlations between the insulin delivery data, the glucose measurement data, and the user feedback data for the different potential insertion sites, along with usage data characterizing the duration and frequency of usage of the potential insertion sites, the remote device or service may generate or otherwise provide recommendations or other indicia of suggested insertion sites or other analysis or evaluation of the health of one or more potential insertion sites. In some embodiments, the remote device or service may also perform predictions or other forward-looking analysis to provide feedback or indicia of the predicted effectiveness our probable outcome of using a particular insertion site.

In addition to the tracking algorithm and corresponding recommendations or feedback pertaining to insertion site performance, some exemplary embodiments also employ a healing algorithm in concert with the tracking and performance analysis to provide recommendations or other feedback to facilitate insertion site health and maintenance for a patient or other user attempting to select a potential insertion site to be utilized. Various embodiments may also provide predictive suggestions for different types of insertable medical devices or insertable elements to be utilized (e.g., a recommended type of infusion set), or provide predictive warnings regarding possible detachment or other observed trends in the data collected for the patient.

FIG. 1 depicts one exemplary embodiment of an infusion system 100 that includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like. In exemplary embodiments, the infusion device 102 includes or is otherwise associated with an insertable element, such as a fluid delivery needle or cannula, which may be inserted into the body of a user and affixed or otherwise adhered to the skin of the user, for example, using an adhesive. In some embodiments, the insertable element associated with the infusion device 102 is in fluid communication with the reservoir housed within the main body or housing of the infusion device 102 via tubing to establish a fluid delivery path from the reservoir to the body of the user via the tubing and cannula.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos.: 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
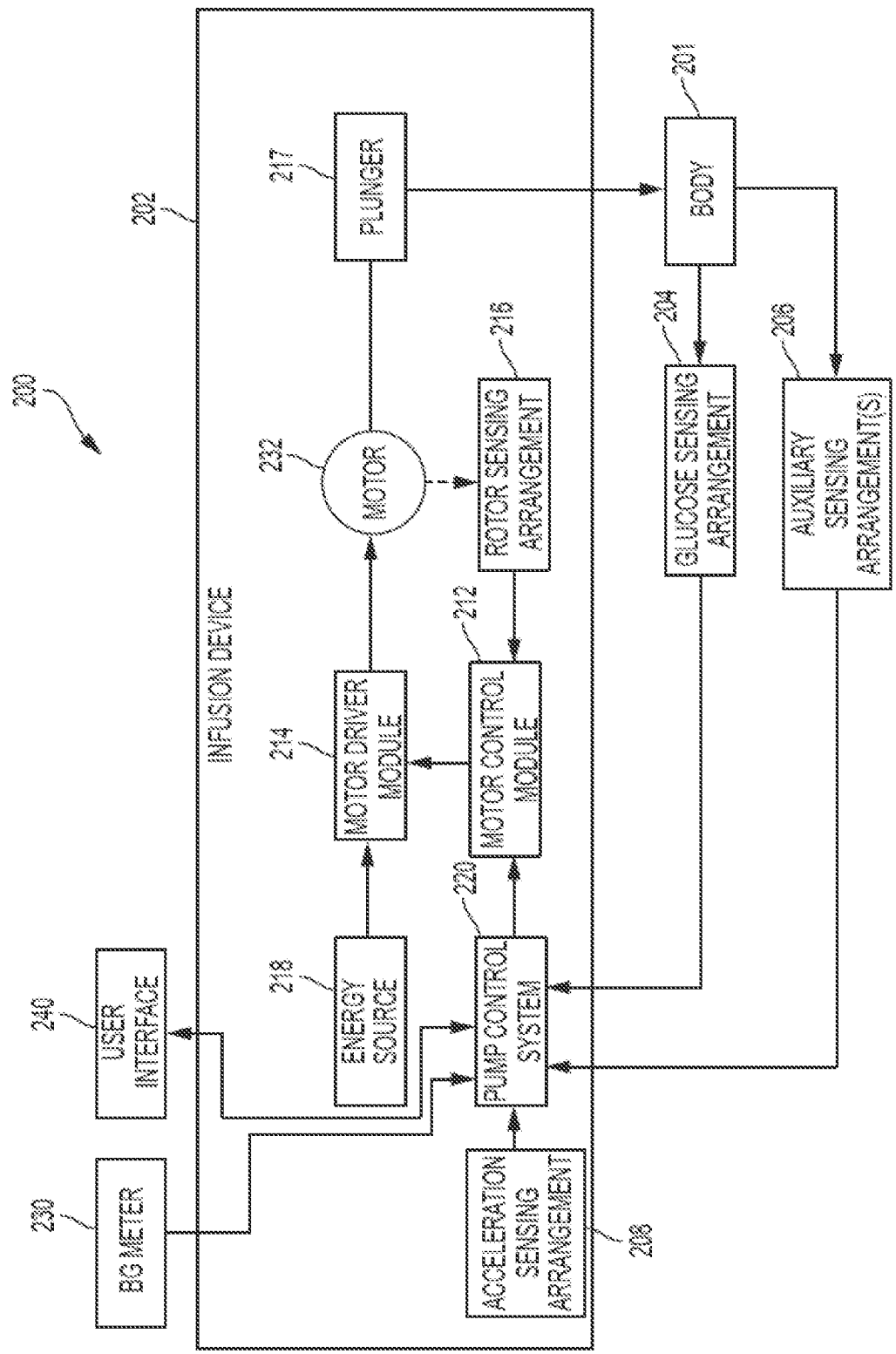
FIG. 2 is a block diagram of an exemplary control system suitable for use with a fluid infusion device in one or more embodiments.

FIG. 2 depicts an exemplary embodiment of a control system 200 suitable for use with an infusion device 202, such as the infusion device 102 described above. The control system 200 is capable of controlling or otherwise regulating a physiological condition in the body 201 of a patient to a desired (or target) value or otherwise maintain the condition within a range of acceptable values in an automated or autonomous manner. In one or more exemplary embodiments, the condition being regulated is sensed, detected, measured or otherwise quantified by a sensing arrangement 204 (e.g., sensing arrangement 104) communicatively coupled to the infusion device 202. However, it should be noted that in alternative embodiments, the condition being regulated by the control system 200 may be correlative to the measured values obtained by the sensing arrangement 204. That said, for clarity and purposes of explanation, the subject matter may be described herein in the context of the sensing arrangement 204 being realized as a glucose sensing arrangement that senses, detects, measures or otherwise quantifies the patient's glucose level, which is being regulated in the body 201 of the patient by the control system 200.

In exemplary embodiments, the sensing arrangement 204 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 201 of the patient. The output electrical signals are filtered or otherwise processed to obtain a measurement value indicative of the patient's interstitial fluid glucose level. In exemplary embodiments, a blood glucose meter 230, such as a finger stick device, is utilized to directly sense, detect, measure or otherwise quantify the blood glucose in the body 201 of the patient. In this regard, the blood glucose meter 230 outputs or otherwise provides a measured blood glucose value that may be utilized as a reference measurement for calibrating the sensing arrangement 204 and converting a measurement value indicative of the patient's interstitial fluid glucose level into a corresponding calibrated blood glucose value. For purposes of explanation, the calibrated blood glucose value calculated based on the electrical signals output by the sensing element(s) of the sensing arrangement 204 may alternatively be referred to herein as the sensor glucose value, the sensed glucose value, or variants thereof.

In the illustrated embodiment, the control system 200 also includes one or more additional sensing arrangements 206, 208 configured to sense, detect, measure or otherwise quantify a characteristic of the body 201 of the patient that is indicative of a condition in the body 201 of the patient. In this regard, in addition to the glucose sensing arrangement 204, one or more auxiliary sensing arrangements 206 may be worn, carried, or otherwise associated with the body 201 of the patient to measure characteristics or conditions of the patient (or the patient's activity) that may influence the patient's glucose levels or insulin sensitivity. For example, a heart rate sensing arrangement 206 could be worn on or otherwise associated with the patient's body 201 to sense, detect, measure or otherwise quantify the patient's heart rate, which, in turn, may be indicative of exercise (and the intensity thereof) that is likely to influence the patient's glucose levels or insulin response in the body 201. In yet another embodiment, another invasive, interstitial, or subcutaneous sensing arrangement 206 may be inserted into the body 201 of the patient to obtain measurements of another physiological condition that may be indicative of exercise (and the intensity thereof), such as, for example, a lactate sensor, a ketone sensor, or the like. Depending on the embodiment, the auxiliary sensing arrangement(s) 206 could be realized as a standalone component worn by the patient, or alternatively, the auxiliary sensing arrangement(s) 206 may be integrated with the infusion device 202 or the glucose sensing arrangement 204.

The illustrated control system 200 also includes an acceleration sensing arrangement 208 (or accelerometer) that may be worn on or otherwise associated with the patient's body 201 to sense, detect, measure or otherwise quantify an acceleration of the patient's body 201, which, in turn, may be indicative of exercise or some other condition in the body 201 that is likely to influence the patient's insulin response.

While the acceleration sensing arrangement 208 is depicted as being integrated into the infusion device 202 in FIG. 2, in alternative embodiments, the acceleration sensing arrangement 208 may be integrated with another sensing arrangement 204, 206 on the body 201 of the patient, or the acceleration sensing arrangement 208 may be realized as a separate standalone component that is worn by the patient.

In some embodiments, the infusion device 202 (or the control system 200) may also include one or more environmental sensing arrangements to sense, detect, measure or otherwise quantify the current operating environment around the infusion device 202. In this regard, the environmental sensing arrangements may include one or more of a temperature sensing arrangement (or thermometer), a humidity sensing arrangement, a pressure sensing arrangement (or barometer), and/or the like. Additionally, the infusion device 202 (or the control system 200) may also include a position sensing arrangement to sense, detect, measure or otherwise quantify the current geographic location of the infusion device 202, such as, for example, a global positioning system (GPS) receiver. Again, it should be noted that such sensing arrangements could be integrated into the infusion device 202, integrated with other components, or realized as separate standalone components that are worn or carried by the patient.

In the illustrated embodiment, the pump control system 220 generally represents the electronics and other components of the infusion device 202 that control operation of the fluid infusion device 202 according to a desired infusion delivery program in a manner that is influenced by the sensed glucose value indicating the current glucose level in the body 201 of the patient. For example, to support a closed-loop operating mode, the pump control system 220 maintains, receives, or otherwise obtains a target or commanded glucose value, and automatically generates or otherwise determines dosage commands for operating an actuation arrangement, such as a motor 232, to displace the plunger 217 and deliver insulin to the body 201 of the patient based on the difference between the sensed glucose value and the target glucose value. In other operating modes, the pump control system 220 may generate or otherwise determine dosage commands configured to maintain the sensed glucose value below an upper glucose limit, above a lower glucose limit, or otherwise within a desired range of glucose values. In practice, the infusion device 202 may store or otherwise maintain the target value, upper and/or lower glucose limit(s), insulin delivery limit(s), and/or other glucose threshold value(s) in a data storage element accessible to the pump control system 220. As described in greater detail, in one or more exemplary embodiments, the pump control system 220 automatically adjusts or adapts one or more parameters or other control information used to generate commands for operating the motor 232 in a manner that accounts for a likely change in the patient's glucose level or insulin response resulting from a meal, exercise, or other activity.

Still referring to FIG. 2, the target glucose value and other threshold glucose values utilized by the pump control system 220 may be received from an external component (e.g., CCD 106 and/or computing device 108) or be input by a patient via a user interface element 240 associated with the infusion device 202. In practice, the one or more user interface element(s) 240 associated with the infusion device 202 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 240 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the patient. It should be noted that although FIG. 2 depicts the user interface element(s) 240 as being separate from the infusion device 202, in practice, one or more of the user interface element(s) 240 may be integrated with the infusion device 202. Furthermore, in some embodiments, one or more user interface element(s) 240 are integrated with the sensing arrangement 204 in addition to and/or in alternative to the user interface element(s) 240 integrated with the infusion device 202. The user interface element(s) 240 may be manipulated by the patient to operate the infusion device 202 to deliver correction boluses, adjust target and/or threshold values, modify the delivery control scheme or operating mode, and the like, as desired.

Still referring to FIG. 2, in the illustrated embodiment, the infusion device 202 includes a motor control module 212 coupled to a motor 232 that is operable to displace a plunger 217 in a reservoir and provide a desired amount of fluid to the body 201 of a patient. In this regard, displacement of the plunger 217 results in the delivery of a fluid, such as insulin, that is capable of influencing the patient's physiological condition to the body 201 of the patient via a fluid delivery path (e.g., via tubing of an infusion set). A motor driver module 214 is coupled between an energy source 218 and the motor 232. The motor control module 212 is coupled to the motor driver module 214, and the motor control module 212 generates or otherwise provides command signals that operate the motor driver module 214 to provide current (or power) from the energy source 218 to the motor 232 to displace the plunger 217 in response to receiving, from a pump control system 220, a dosage command indicative of the desired amount of fluid to be delivered.

In exemplary embodiments, the energy source 218 is realized as a battery housed within the infusion device 202 that provides direct current (DC) power. In this regard, the motor driver module 214 generally represents the combination of circuitry, hardware and/or other electrical components configured to convert or otherwise transfer DC power provided by the energy source 218 into alternating electrical signals applied to respective phases of the stator windings of the motor 232 that result in current flowing through the stator windings that generates a stator magnetic field and causes the rotor of the motor 232 to rotate. The motor control module 212 is configured to receive or otherwise obtain a commanded dosage from the pump control system 220, convert the commanded dosage to a commanded translational displacement of the plunger 217, and command, signal, or otherwise operate the motor driver module 214 to cause the rotor of the motor 232 to rotate by an amount that produces the commanded translational displacement of the plunger 217. For example, the motor control module 212 may determine an amount of rotation of the rotor required to produce translational displacement of the plunger 217 that achieves the commanded dosage received from the pump control system 220. Based on the current rotational position (or orientation) of the rotor with respect to the stator that is indicated by the output of the rotor sensing arrangement 216, the motor control module 212 determines the appropriate sequence of alternating electrical signals to be applied to the respective phases of the stator windings that should rotate the rotor by the determined amount of rotation from its current position (or orientation). In embodiments where the motor 232 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 212 operates the motor driver module 214 to apply the determined alternating electrical signals (e.g., the command signals) to the stator windings of the motor 232 to achieve the desired delivery of fluid to the patient.

When the motor control module 212 is operating the motor driver module 214, current flows from the energy source 218 through the stator windings of the motor 232 to produce a stator magnetic field that interacts with the rotor magnetic field. In some embodiments, after the motor control module 212 operates the motor driver module 214 and/or motor 232 to achieve the commanded dosage, the motor control module 212 ceases operating the motor driver module 214 and/or motor 232 until a subsequent dosage command is received. In this regard, the motor driver module 214 and the motor 232 enter an idle state during which the motor driver module 214 effectively disconnects or isolates the stator windings of the motor 232 from the energy source 218. In other words, current does not flow from the energy source 218 through the stator windings of the motor 232 when the motor 232 is idle, and thus, the motor 232 does not consume power from the energy source 218 in the idle state, thereby improving efficiency.

Depending on the embodiment, the motor control module 212 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 212 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 212. The computer-executable programming instructions, when read and executed by the motor control module 212, cause the motor control module 212 to perform or otherwise support the tasks, operations, functions, and processes described herein.

It should be appreciated that FIG. 2 is a simplified representation of the infusion device 202 for purposes of explanation and is not intended to limit the subject matter described herein in any way. In this regard, depending on the embodiment, some features and/or functionality of the sensing arrangement 204 may be implemented by or otherwise integrated into the pump control system 220, or vice versa. Similarly, in practice, the features and/or functionality of the motor control module 212 may be implemented by or otherwise integrated into the pump control system 220, or vice versa. Furthermore, the features and/or functionality of the pump control system 220 may be implemented by control electronics located in the fluid infusion device 202, while in alternative embodiments, the pump control system 220 may be implemented by a remote computing device that is physically distinct and/or separate from the infusion device 202, such as, for example, the CCD 106 or the computing device 108.

Figure 3:
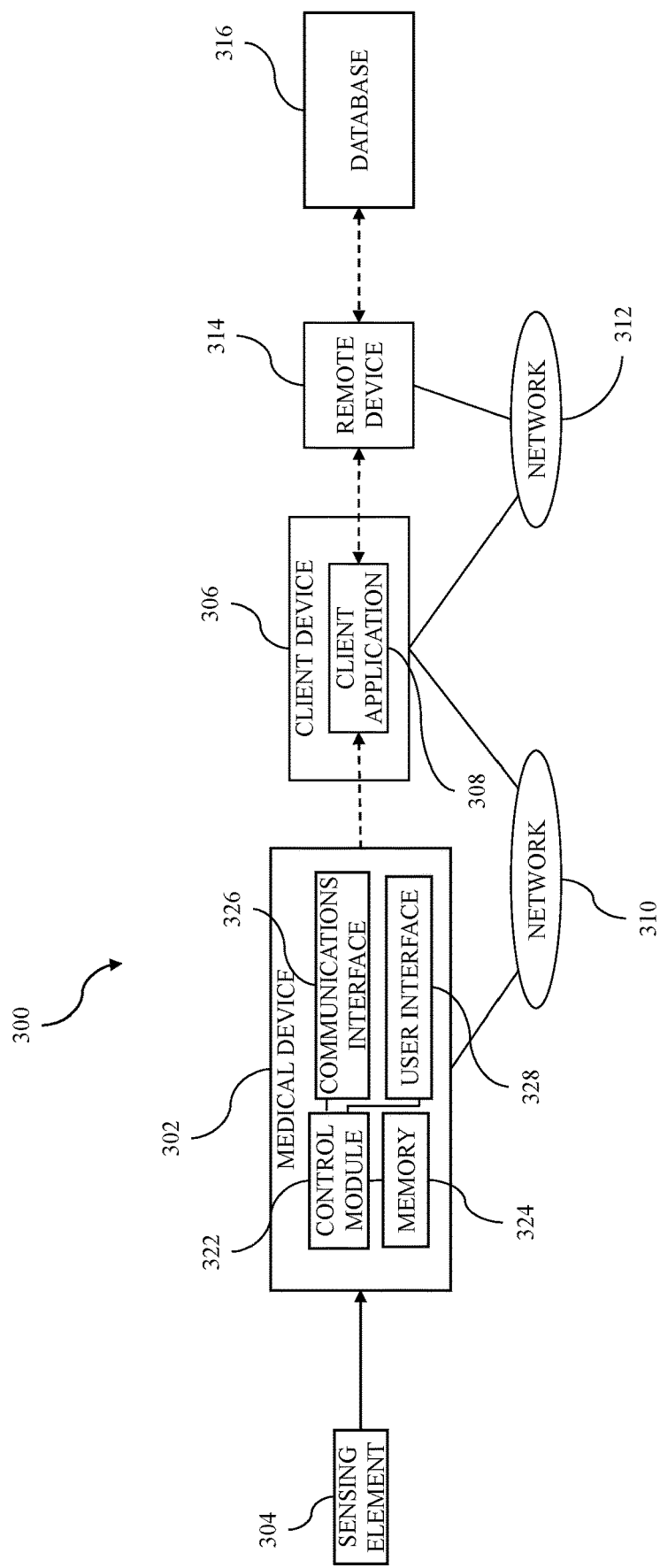
FIG. 3 is a block diagram of an exemplary patient monitoring system.

FIG. 3 depicts an exemplary embodiment of a patient monitoring system 300. The patient monitoring system 300 includes a medical device 302 that is communicatively coupled to a sensing element 304 that is inserted into the body of a patient or otherwise worn by the patient to obtain measurement data indicative of a physiological condition in the body of the patient, such as a sensed glucose level. In the illustrated embodiment, the medical device 302 is communicatively coupled to a client device 306 via a communications network 310, with the client device 306 being communicatively coupled to a remote device 314 via another communications network 312. In this regard, the client device 306 may function as an intermediary for uploading or otherwise providing measurement data from the medical device 302 to the remote device 314. It should be appreciated that FIG. 3 depicts a simplified representation of a patient monitoring system 300 for purposes of explanation and is not intended to limit the subject matter described herein in any way. For example, some embodiments may support direct communications between the medical device 302 and the remote device 314 via communications network 312.

In exemplary embodiments, the client device 306 is realized as a mobile phone, a smartphone, a tablet computer, or other similar mobile electronic device; however, in other embodiments, the client device 306 may be realized as any sort of electronic device capable of communicating with the medical device 302 via network 310, such as a laptop or notebook computer, a desktop computer, or the like. In exemplary embodiments, the network 310 is realized as a Bluetooth network, a ZigBee network, or another suitable personal area network. That said, in other embodiments, the network 310 could be realized as a wireless ad hoc network, a wireless local area network (WLAN), or local area network (LAN). The client device 306 includes or is coupled to a display device, such as a monitor, screen, or another conventional electronic display, capable of graphically presenting data and/or information pertaining to the physiological condition of the patient. The client device 306 also includes or is otherwise associated with a user input device, such as a keyboard, a mouse, a touchscreen, or the like, capable of receiving input data and/or other information from the user of the client device 306.

In some embodiments, a user, such as the patient, the patient's doctor or another healthcare provider, or the like, manipulates the client device 306 to execute a client application 308 that supports communicating with the medical device 302 via the network 310. In this regard, the client application 308 supports establishing a communications session with the medical device 302 on the network 310 and receiving data and/or information from the medical device 302 via the communications session. The medical device 302 may similarly execute or otherwise implement a corresponding application or process that supports establishing the communications session with the client application 308. The client application 308 generally represents a software module or another feature that is generated or otherwise implemented by the client device 306 to support the processes described herein. Accordingly, the client device 306 generally includes a processing system and a data storage element (or memory) capable of storing programming instructions for execution by the processing system, that, when read and executed, cause processing system to create, generate, or otherwise facilitate the client application 308 and perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In one or more embodiments, the client device 306 and the medical device 302 establish an association (or pairing) with one another over the network 310 to support subsequently establishing a point-to-point communications session between the medical device 302 and the client device 306 via the network 310. For example, in accordance with one embodiment, the network 310 is realized as a Bluetooth network, wherein the medical device 302 and the client device 306 are paired with one another (e.g., by obtaining and storing network identification information for one another) by performing a discovery procedure or another suitable pairing procedure. The pairing information obtained during the discovery procedure allows either of the medical device 302 or the client device 306 to initiate the establishment of a secure communications session via the network 310.

In one or more exemplary embodiments, the client application 308 is also configured to store or otherwise maintain a network address and/or other identification information for the remote device 314 on the second network 312. In this regard, the second network 312 may be physically and/or logically distinct from the network 310, such as, for example, the Internet, a cellular network, a wide area network (WAN), or the like. The remote device 314 generally represents a server or other computing device configured to receive and analyze or otherwise monitor measurement data, event log data, and potentially other information obtained for the patient associated with the medical device 302. In exemplary embodiments, the remote device 314 is coupled to a database 316 configured to store or otherwise maintain data associated with individual patients. In practice, the remote device 314 may reside at a location that is physically distinct and/or separate from the medical device 302 and the client device 306, such as, for example, at a facility that is owned and/or operated by or otherwise affiliated with a manufacturer of the medical device 302. For purposes of explanation, but without limitation, the remote device 314 may alternatively be referred to herein as a server.

It should be noted that in some embodiments, some or all of the functionality and processing intelligence of the remote computing device 314 can reside at the medical device 302 and/or at other components or computing devices that are compatible with the patient monitoring system 300. In other words, the patient monitoring system 300 need not rely on a network-based or a cloud-based server arrangement as depicted in FIG. 3, although such a deployment might be the most efficient and economical implementation. These and other alternative arrangements are contemplated by this disclosure. To this end, some embodiments of the system 300 may include additional devices and components that serve as data sources, data processing units, and/or recommendation delivery mechanisms. For example, the system 300 may include any or all of the following elements, without limitation: computer devices or systems; patient monitors; healthcare provider systems; data communication devices; and the like.

Still referring to FIG. 3, the sensing element 304 generally represents the component of the patient monitoring system 300 that is configured to generate, produce, or otherwise output one or more electrical signals indicative of a physiological condition that is sensed, measured, or otherwise quantified by the sensing element 304. In this regard, the physiological condition of a patient influences a characteristic of the electrical signal output by the sensing element 304, such that the characteristic of the output signal corresponds to or is otherwise correlative to the physiological condition that the sensing element 304 is sensitive to. In exemplary embodiments, the sensing element 304 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 304.

The medical device 302 generally represents the component of the patient monitoring system 300 that is communicatively coupled to the output of the sensing element 304 to receive or otherwise obtain the measurement data samples from the sensing element 304 (e.g., the measured glucose and characteristic impedance values), store or otherwise maintain the measurement data samples, and upload or otherwise transmit the measurement data to the server 314 via the client device 306. In one or more embodiments, the medical device 302 is realized as an infusion device 102, 202 configured to deliver a fluid, such as insulin, to the body of the patient. That said, in other embodiments, the medical device 302 could be a standalone sensing or monitoring device separate and independent from an infusion device (e.g., sensing arrangement 104, 204), such as, for example, a continuous glucose monitor (CGM), an interstitial glucose sensing arrangement, or similar device. It should be noted that although FIG. 3 depicts the medical device 302 and the sensing element 304 as separate components, in practice, the medical device 302 and the sensing element 304 may be integrated or otherwise combined to provide a unitary device that can be worn by the patient.

In exemplary embodiments, the medical device 302 includes a control module 322, a data storage element 324 (or memory), a communications interface 326, and a user interface 328. The user interface 328 generally represents the input user interface element(s) and/or output user interface element(s) associated with the medical device 302 (e.g., one or more user interface elements 240). The control module 322 generally represents the hardware, circuitry, logic, firmware and/or other component(s) of the medical device 302 that is coupled to the sensing element 304 to receive the electrical signals output by the sensing element 304 and perform or otherwise support various additional tasks, operations, functions and/or processes described herein. Depending on the embodiment, the control module 322 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 322 includes an analog-to-digital converter (ADC) or another similar sampling arrangement that samples or otherwise converts an output electrical signal received from the sensing element 304 into corresponding digital measurement data value. In other embodiments, the sensing element 304 may incorporate an ADC and output a digital measurement value.

The communications interface 326 generally represents the hardware, circuitry, logic, firmware and/or other components of the medical device 302 that are coupled to the control module 322 for outputting data and/or information from/to the medical device 302 to/from the client device 306. For example, the communications interface 326 may include or otherwise be coupled to one or more transceiver modules capable of supporting wireless communications between the medical device 302 and the client device 306. In exemplary embodiments, the communications interface 326 is realized as a Bluetooth transceiver or adapter configured to support Bluetooth Low Energy (BLE) communications.

In exemplary embodiments, the remote device 314 receives, from the client device 306, measurement data values associated with a particular patient (e.g., sensor glucose measurements, acceleration measurements, and the like) that were obtained using the sensing element 304, and the remote device 314 stores or otherwise maintains the historical measurement data in the database 316 in association with the patient (e.g., using one or more unique patient identifiers). Additionally, the remote device 314 may also receive, from or via the client device 306, meal data or other event log data that may be input or otherwise provided by the patient (e.g., via client application 308) and store or otherwise maintain historical meal data and other historical event or activity data associated with the patient in the database 316. In this regard, the meal data include, for example, a time or timestamp associated with a particular meal event, a meal type or other information indicative of the content or nutritional characteristics of the meal, and an indication of the size associated with the meal. In exemplary embodiments, the remote device 314 also receives historical fluid delivery data corresponding to basal or bolus dosages of fluid delivered to the patient by an infusion device 102, 202. For example, the client application 308 may communicate with an infusion device 102, 202 to obtain insulin delivery dosage amounts and corresponding timestamps from the infusion device 102, 202, and then upload the insulin delivery data to the remote device 314 for storage in association with the particular patient. The remote device 314 may also receive geolocation data and potentially other contextual data associated with a device 302, 306 from the client device 306 and/or client application 308, and store or otherwise maintain the historical operational context data in association with the particular patient. In this regard, one or more of the devices 302, 306 may include a global positioning system (GPS) receiver or similar modules, components or circuitry capable of outputting or otherwise providing data characterizing the geographic location of the respective device 302, 306 in real-time.

As described in greater detail below, in exemplary embodiments, the client application 308 provides guidance, recommendations, or other user notifications that facilitate rotation of the insertion site locations utilized in connection with a patient's medical devices 302, 304. For example, when a patient attempts to change or rotate an infusion set, a glucose sensor, and/or the like, the patient may utilize the client application 308 to obtain guidance or recommendations based on the patient's previous or historical usage of insertion sites. The patient utilizes the client application 308 to input or otherwise provide information indicating the type of insertable element or insertable device being utilized at a particular insertion site, the location of the insertion site on the patient's body, and the patient's subjective evaluation of the performance associated with the insertion site. The client application 308 uploads or otherwise transmits the collected user feedback pertaining to the insertion site to the remote device 314, which, in turn, utilizes the insertion site location feedback to associate subsets of the patient's historical glucose measurement data, historical fluid delivery data, and/or historical event log data with a particular insertion site location. In this regard, samples of historical glucose measurement data, historical fluid delivery data and/or historical event log data having associated timestamps that are concurrent to the duration or period of time when a medical device 302, 304 was utilized at a particular insertion site location may be tagged or otherwise associated with that insertion site location.

The relationships between the subsets of historical glucose measurement data, historical fluid delivery data, the historical event log data and/or the subjective user feedback associated with a particular insertion site location may be analyzed to determine one or more metrics indicative of the health or usage of the particular insertion site location. Additionally, the relationships between the subsets of historical glucose measurement data, historical fluid delivery data, the historical event log data and/or the subjective user feedback associated with a particular insertion site location may be utilized to derive one or more performance models for the particular insertion site location. Thereafter, when a patient attempts to change or rotate the insertion site associated with a particular device 302, 304, the client application 308 and/or remote device 314 may calculate or otherwise determine health or usage metrics associated with each potential insertion site. Additionally, the patient-specific performance models may be utilized to calculate or otherwise determine one or more metrics indicative of the probable performance of each potential insertion site. Utilizing the insertion site health metric(s) in concert with the probable performance metric(s), the client application 308 and/or remote device 314 may identify one or more potential insertion sites for recommendation and provide graphical indicia of the recommended insertion sites. Likewise, the client application 308 and/or remote device 314 may identify one or more potential insertion sites to be avoided, for example, when the health or usage metrics indicate overuse of the insertion site or the performance metrics indicate a potential loss of effectiveness of the insertion site.

Figure 4:
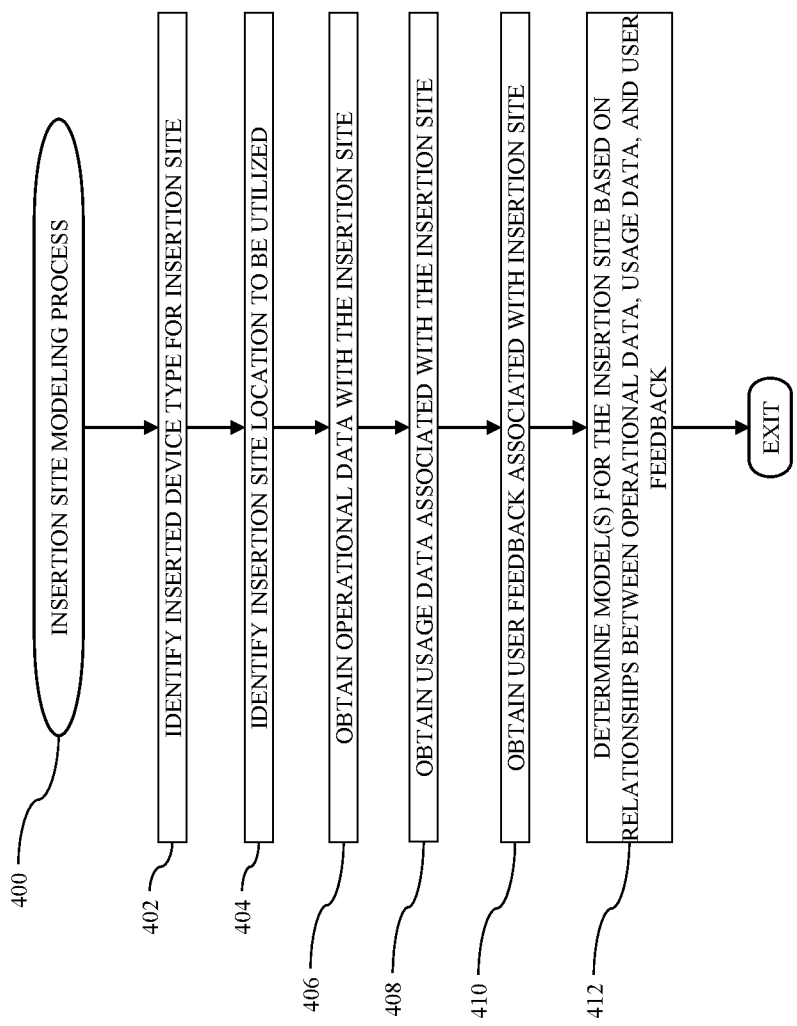
FIG. 4 is a flow diagram of an exemplary insertion site modeling process in one or more exemplary embodiments.

FIG. 4 depicts an exemplary insertion site modeling process 400 suitable for determining one or more models for the performance or health associated with different insertion site locations. The various tasks performed in connection with the insertion site monitoring process 400 may be performed by hardware, firmware, software executed by processing circuitry, or any combination thereof. For illustrative purposes, the following description refers to elements mentioned above in connection with FIGS. 1-3. In practice, portions of the insertion site modeling process 400 may be performed by different elements of a patient monitoring system, however, for purposes of explanation, the insertion site modeling process 400 may be described herein primarily in the context of the client device 306, the client application 308 and/or the remote device 314. It should be appreciated that the insertion site modeling process 400 may include any number of additional or alternative tasks, the tasks need not be performed in the illustrated order and/or the tasks may be performed concurrently, and/or the insertion site modeling process 400 may be incorporated into a more comprehensive procedure or process having additional functionality not described in detail herein. Moreover, one or more of the tasks shown and described in the context of FIG. 4 could be omitted from a practical embodiment of the insertion site modeling process 400 as long as the intended overall functionality remains intact.

Referring to FIG. 4, with continued reference to FIGS. 1-3, the illustrated insertion site modeling process 400 identifies the particular type of medical device or insertable element to be inserted and the insertion site location on the body to be utilized (task 402, 404). In this regard, whenever a patient inserts a needle, cannula, or other insertable element associated with a medical device at a particular location on his or her body, the patient may utilize the client application 308 on the client device 306 (or CCD 106) to input or otherwise provide identification of the location on his or her body where the insertion occurred along with an indication of the type of medical device being utilized with the insertion site location.

Figure 5:
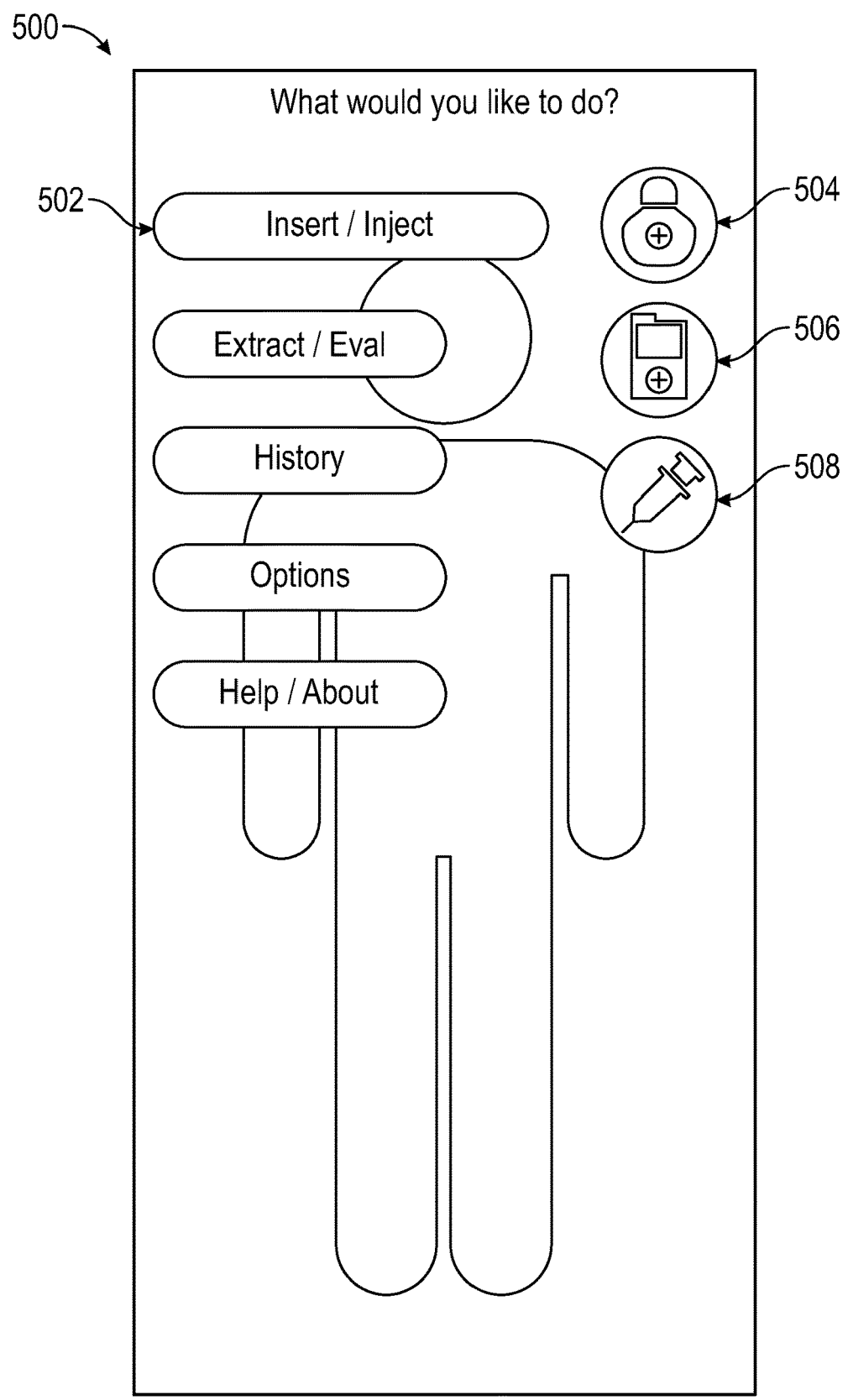
FIGS. 5-8 depict exemplary graphical user interface (GUI) displays suitable for presentation in connection with the insertion site modeling process of FIG. 4 in one or more exemplary embodiments.
Figure 6:
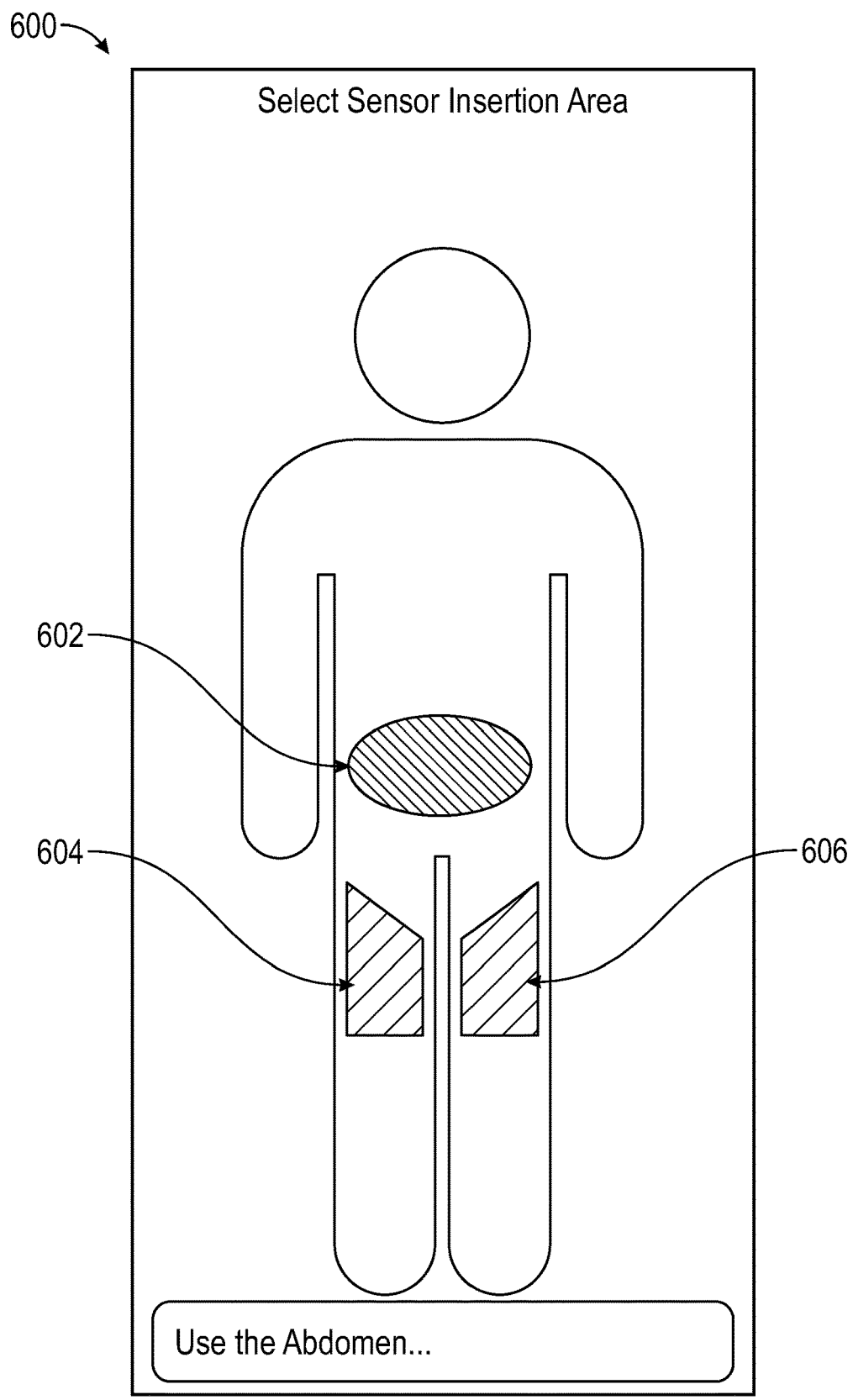
Figure 7:
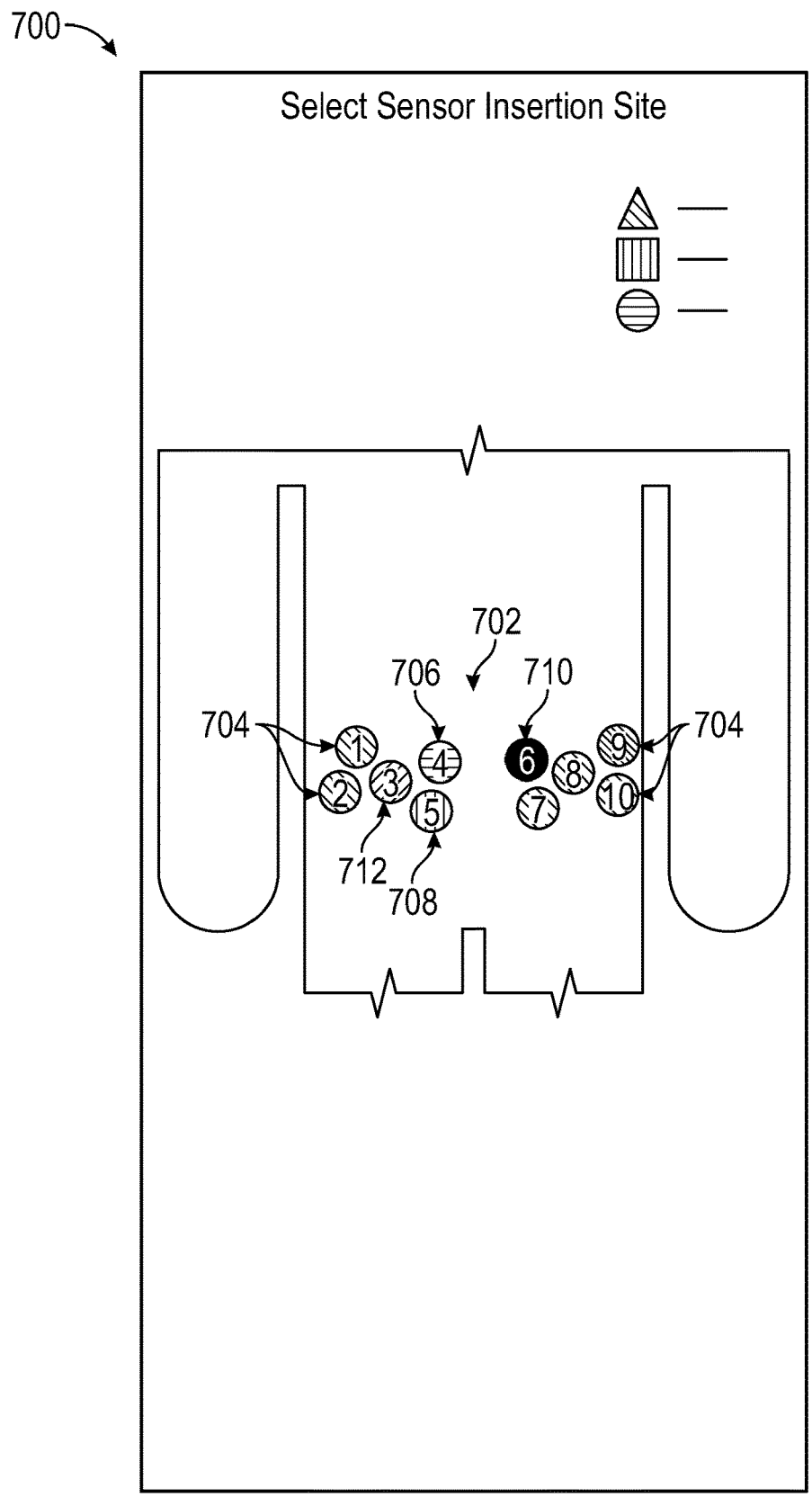

FIGS. 5-7 depict an exemplary sequence of graphical user interface (GUI) displays that may be generated or otherwise provided by the client application 308 on the client device 306 in connection with the insertion site modeling process 400 to identify the insertion site location and type of insertable device to be utilized prior to obtaining data pertaining the patient's physiological condition and the performance of the insertion site location. A patient may launch or otherwise navigate the client application 308 on the client device 306 to a home screen GUI display 500 that includes a button or similar selectable GUI element 502 that the patient may select to indicate a desire to perform a new insertion or injection. In response to selection of the insertion/injection GUI element 502, the client application 308 dynamically updates the home screen GUI display 500 to include additional selectable GUI elements 504, 506, 508 that allow the patient to identify whether the patient would like to perform an insertion associated with a sensor (e.g., sensor button 504), an insertion associated with an infusion device (e.g., infusion device button 506), or an insertion associated with an injection (e.g., injection button 508).

Referring to FIG. 6, in response to selection of the particular type of insertion to be performed via one of the GUI elements 504, 506, 508, the client application 308 generates or otherwise provides a body region selection GUI display 600 that includes a graphical representation of a body of the patient having selectable body regions 602, 604, 606 corresponding to potential locations where the patient can perform the insertion. For example, in response to selection of the sensor button 504 to insert an interstitial glucose sensing element 104, 204, 304, the client application 308 provides selectable overlay regions 602, 604, 606 on the graphical representation of the body corresponding to the abdomen region 602 and the upper legs 604, 606. The overlays 602, 604, 606 may be rendered using one or more visually distinguishable characteristics to provide guidance, suggestions, or recommendations for which region(s) should be utilized by the patient, for example, to achieve optimal performance, optimize site health, and/or the like. For example, the abdomen region overlay 602 may be rendered using green or another color or visually distinguishable characteristic to indicate the abdomen region is recommended or otherwise preferred, with the upper leg region overlays 604, 606 being rendered using yellow or another color or visually distinguishable characteristic to indicate those regions are less preferable.

Referring now to FIG. 7, in response to selection of a body region for the insertion, the client application 308 generates or otherwise provides a site selection GUI display 700 that includes an enhanced or zoomed view of the selected body region that includes graphical indicia of the potential insertion site locations for that selected body region. For example, in response to selection of the abdomen region overlay 602, the client application 308 generates the site selection GUI display 700 that includes a zoomed or enhanced graphical representation of the abdomen along with selectable graphical indicia 702 corresponding to the different potential insertion site locations in the abdomen region of the body. Similar to the body regions, the graphical indicia of the insertion site locations may be color-coded or otherwise rendered using different visually distinguishable characteristics to provide guidance to the patient regarding the state of the differential insertion site locations. For example, as described in greater detail below, based on various health, usage, or performance metrics associated with a respective insertion site location, the client application 308 and/or remote device 314 may classify or otherwise categorize each respective insertion site location into a particular class or category of viability.

For example, in one embodiment, potential insertion site locations having health or usage metrics that indicate they have not been overused or at risk of site loss while also having performance metrics that indicate they achieve adequate performance may be classified into a high viability category and have their corresponding indicia 704 rendered using green or another color or visually distinguishable characteristic to convey a relatively high viability state. On the other hand, potential insertion site locations having health or usage metrics that indicate they have been used too recently or have not had adequate time to heal or recover after a previous usage may be classified into another category and have their corresponding indicia 706 rendered using red or another color or visually distinguishable characteristic to indicate those site locations should be avoided. Potential insertion site locations that have one or more problematic performance metrics may be classified into an intermediate viability category and have their corresponding indicia 708 rendered using yellow or another visually distinguishable characteristic to indicate a higher level of caution should be associated with those site locations. Any insertion site locations that have exhibited performance metrics indicative of site loss may be classified into a lost site category and have their corresponding indicia 710 rendered using black or another visually distinguishable characteristic to indicate those site locations are unusable. Any insertion site locations that are actively in use with another device may also have their indicia 712 be rendered using a color or other visually distinguishable characteristic to indicate temporary unavailability of those site locations.

The patient may utilize the site selection GUI display 700 to choose the insertion site location to be utilized and then input the selected site location by selecting the button or similar selectable GUI element 702 corresponding to the selected site location. In response to receiving indication of the selected site location, the client application 308 may transmit or otherwise provide indication of the selected insertion site location and the type of device associated with the insertion site location to the remote device 314 for tracking or otherwise monitoring the duration of use of the insertion site location and the particular insertable devices used at that insertion site location.

Referring again to FIG. 4, the insertion site modeling process 400 continues by receiving or otherwise obtaining operational data associated with the current usage of the insertion site (task 406). In this regard, the client application 308 and/or remote device 314 receives sensed glucose measurement data and/or insulin delivery data from the patient's medical device(s) 302, 304 and utilizes the timestamps associated with the obtained data samples to associate the patient's data indicative of the performance of the insertion site(s) with the insertion site location used concurrent to collection of those data samples. The client application 308 and/or remote device 314 may also obtain activity data or other event log data for the patient (e.g., meal data, exercise data, sleep data, and/or the like) and associate the data pertaining to the patient's activities while a particular insertion site location is being utilized to that particular insertion site location. In this manner, the remote device 314 may associate subsets of the patient's historical data maintained in the database 316 with the particular insertion site location(s) utilized concurrent to when samples or pieces of the respective subsets of data were obtained. Thus, sensed glucose measurement data samples output by the sensing device 304 during the period of time the insertable element of the sensing device 304 is inserted at a particular insertion site location are maintained in association with that insertion site location, dosages of insulin delivered by the infusion device 302 during the period of time the cannula of the infusion set is inserted at a particular insertion site location are maintained in association with that insertion site location, and so on. The glucose measurement data, insulin delivery data, and other data indicative of the performance of a respective insertion site location may be utilized to calculate or otherwise determine one or more performance metrics associated with a particular insertion site location or combination of insertion site locations, such as, for example, the time in range or percentage of time the patient's sensed glucose measurement values are within target range of glucose values for the patient (e.g., between 80 mg/dL and 140 mg/dL), the percentage of time the patient's sensor glucose measurement values are outside of the target range, the mean or median sensor glucose measurement value, the standard deviation associated with the sensor glucose measurement value, the mean or median insulin infusion rate or insulin dosage value, the standard deviation associated with insulin infusion rate or insulin dosages, and/or the like.

The insertion site modeling process 400 also identifies or otherwise obtains usage data associated with the current insertion site location (task 408). For example, the client application 308 may implement a timer or similar features to track the duration of the time periods during which the insertion site location is utilized. The client application 308 may also track usage data including the time of day, the day of the week, and/or the like during which the insertion site location is utilized. The usage data may be utilized to calculate or otherwise determine various usage metrics for the insertion site location, such as, for example, the frequency of use of the insertion site location relative to other insertion site locations, the duration or amount of time between uses of the insertion site location, and/or the like.

Figure 8:
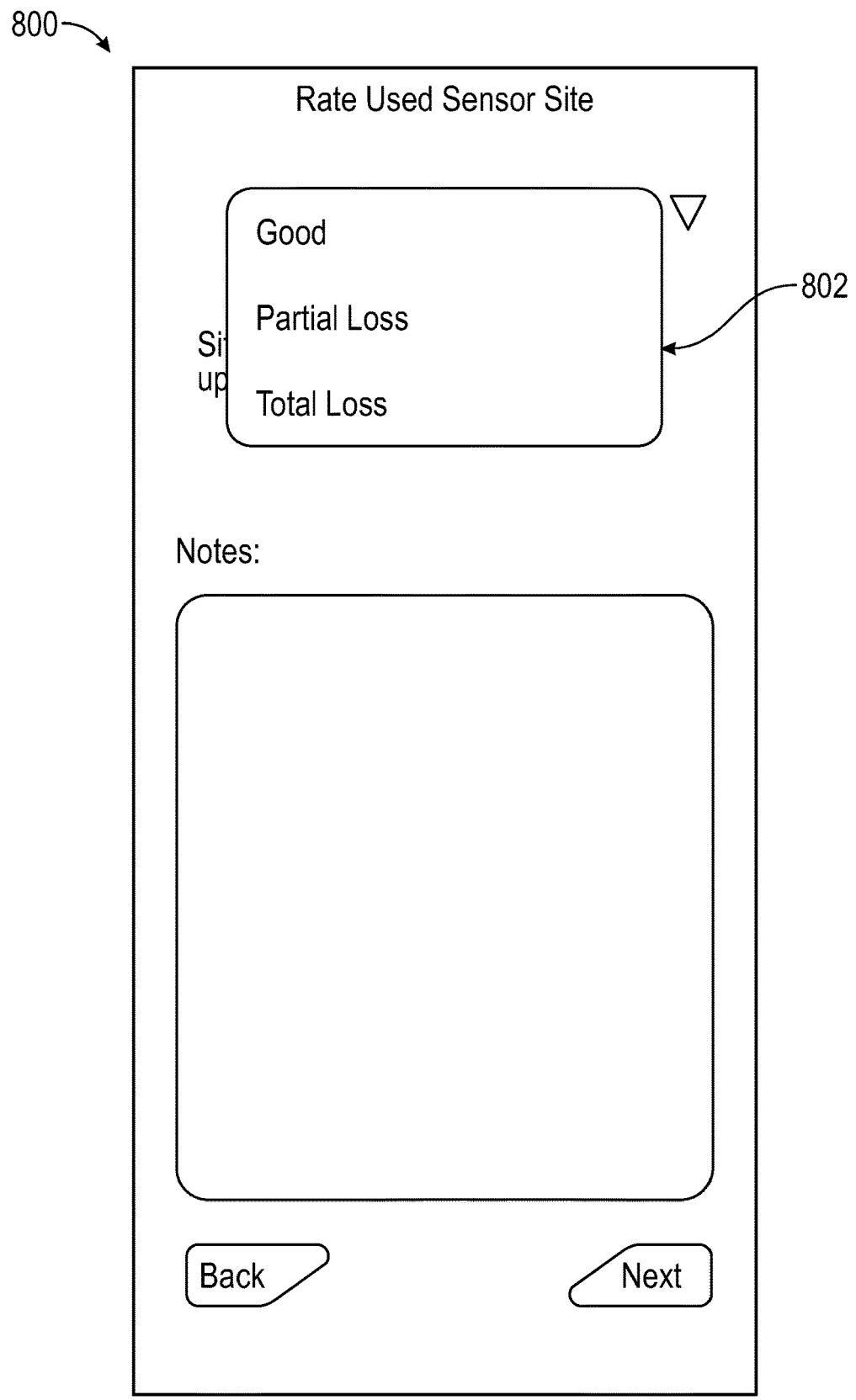

Still referring to FIG. 4 with reference to FIG. 8, in exemplary embodiments, the insertion site modeling process 400 also receives or otherwise obtains user feedback associated with the current insertion site location (task 410). For example, when the patient subsequently interacts with the client application 308 to change, replace, rotate or otherwise cease usage of the insertable element, the client application 308 may provide a feedback collection GUI display 800 at the client device 306 that includes one or more GUI elements that allow the patient to provide his or her subjective assessment of the performance of the insertion site location or other feedback characterizing the state of the insertion site location. The illustrated GUI display 800 includes a pull-down menu 802 or similar GUI element that allows the patient to rate, select or otherwise indicate the perceived performance of the insertion site location from within a list of potential classifications for the insertion site. For example, the illustrated pull-down menu 802 prompts the patient to rate the insertion site as exhibiting good or normal performance, exhibiting partial site loss, or exhibiting total site loss. The subjective patient feedback data collected by the client application 308 may be uploaded or otherwise transmitted to the remote device 314 for analyzing of the insertion site location in conjunction with the performance data or other operational data associated with the insertion site location.

Once an insertion site has been utilized and the patient reengages the client application 308 for moving or rotating to a new insertion site, the client application 308 may assist the patient in finding a new site before prompting the patient for feedback regarding the most recently used site. The client application 308 may prompt the patient to manually classify the most recently used site. If the patient chooses a category indicating adverse or poor performance or potential site loss, the client application 308 may prompt the patient for more information, for example, by providing one or more GUI elements that allow the patient to select, identify, or otherwise indicate symptoms, events, or other problems associated with the insertion site from among one or more listings of potential issues that are commonly experienced or otherwise likely. The GUI display may also provide an option for "other" that allows the patient to manually note or otherwise define the issues experienced. The client application 308 may persist the manually assigned classification and notes or other feedback associated with the site for subsequent presentation to the patient. For example, the client application 308 may depict the site with the color-coding corresponding to the category to which it was manually assigned, and selecting or hovering over the color-coded graphical representation of the site location may result in the client application 308 graphically depicting the notes or other feedback associated with the site that was collected after its most recent usage.

In embodiments where the client application 308 is used in connection with an infusion device 102, 202, 302 and a glucose sensor 104, 204, 304 as part of an infusion system, the various devices may communicate to provide information to the client application 308 in real-time, such as, for example, notification or indicia of events being experienced by the patient in connection with a current insertion site (e.g., hyperglycemic or hypoglycemic alerts, delivery alerts, and/or the like). In this manner, the client application 308 may automatically obtain and populate feedback fields associated with a particular insertion site based on information received from other devices in an infusion system. The event data, alert data, and/or other information received by the tracking application may also be utilized to automatically classify or categorize a particular insertion site.

Referring again to FIG. 4, after obtaining operational data, usage data, and subjective user feedback data for the insertion site location, the insertion site modeling process 400 calculates, determines, or otherwise derives one or more models for the particular insertion site location for the inserted device type based on relationships between the operational data, the usage data, and the subjective user feedback data (task 412). In this regard, in exemplary embodiments, the remote device 314 utilizes machine learning, artificial intelligence or other analytical techniques to determine which combination of glucose measurement data, glucose measurement metrics, insulin delivery data, insulin delivery metrics, activity or event log data, usage data, usage metrics, and/or the like are correlated to or predictive of the health or performance of the insertion site location for the type of inserted device. For example, the remote device 314 may analyze the relationship between the time in range for the patient's sensor glucose measurement value for a particular insertion site location and other variables or parameters to determine a corresponding equation, function, or model for calculating a probable or expected time in range based on a correlative subset usage variables (e.g., duration of time between uses, frequency of use, duration of use, and/or the like). As another example, the remote device 314 may determine a corresponding equation, function, or model for calculating a probable or expected basal insulin infusion rate based on a correlative subset usage variables (e.g., duration of time between uses, frequency of use, duration of use, and/or the like). As yet another example, the remote device 314 may determine a corresponding equation, function, or model for calculating a health metric for the insertion site. For example, sensor glucose measurement data for different fasting periods for the insertion site may be analyzed to derive an equation for calculating a probability of an insertion site loss condition based on a correlative subset usage variables and glucose measurement variables. In this regard, the derived models are capable of characterizing or mapping any particular combination or subset of input variables to a probable performance or health associated with a particular insertion site for a particular type of device. In this regard, the subject matter described herein is not limited to any particular type or number of models that may be derived and utilized, either individually or in combination.

In one or more embodiments, the client application 308 and/or the remote device 314 may also calculate, determine, or otherwise derive, for each potential combination of insertion site and insertable device, a patient-specific glucose forecasting model. For example, artificial intelligence, or other analytical techniques may be utilized to determine a corresponding equation, function, or model for calculating the future glucose values for the patient based on the subsets of the patient's historical insulin delivery data, historical event log data, historical site usage data, and other historical or contextual data are associated with the particular insertion site and insertable device and correlated to or predictive of the historical sensor glucose measurement data. In this regard, the patient-specific and site-specific glucose forecasting model may account for the usage data associated with the insertion site (e.g., the duration of use, frequency of use, time between uses, and the like), so that the usage of the insertion site location influences the resulting glucose predictions. Thus, as an insertion site becomes overused, the glucose predictions may exhibit reduced time in range, higher time out of range, higher variability, or other potentially undesirable outcomes, while glucose predictions for less frequently used or healthier insertion sites may exhibit higher time in range, lower time out of range, less variability, or other potentially desirable attributes.

Still referring to FIG. 4, in exemplary embodiments, the insertion site modeling process 400 is repeated whenever a new insertion is performed or a previous insertion is terminated. In this regard, the various models for insertion site performance and insertion site health may be periodically and dynamically updated to reflect changes with respect to the insertion sites and the patient's physiological condition.

Figure 9:
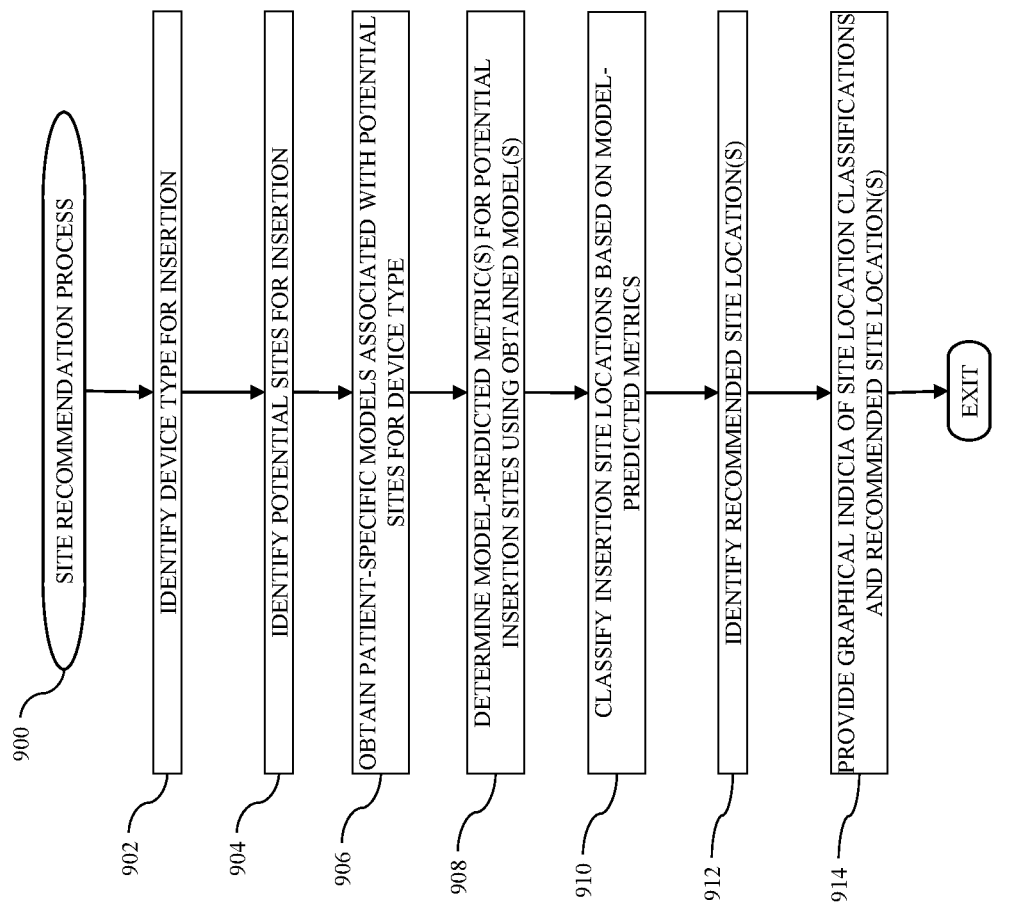
FIG. 9 is a flow diagram of an exemplary insertion site recommendation process suitable for implementation in connection with the insertion site modeling process of FIG. 4 and the GUI displays depicted in FIGS. 5-8 in one or more exemplary embodiments.

FIG. 9 depicts an exemplary insertion site recommendation process 900 suitable for implementation in connection with the site modeling process 400 to provide recommendations or other guidance to facilitate insertion site management. The various tasks performed in connection with the insertion site recommendation process 900 may be performed by hardware, firmware, software executed by processing circuitry, or any combination thereof. For illustrative purposes, the following description refers to elements mentioned above in connection with FIGS. 1-3. In practice, portions of the insertion site recommendation process 900 may be performed by different elements of a patient monitoring system, however, for purposes of explanation, the insertion site recommendation process 900 may be described herein primarily in the context of the client device 306, the client application 308 and/or the remote device 314. It should be appreciated that the insertion site recommendation process 900 may include any number of additional or alternative tasks, the tasks need not be performed in the illustrated order and/or the tasks may be performed concurrently, and/or the insertion site recommendation process 900 may be incorporated into a more comprehensive procedure or process having additional functionality not described in detail herein. Moreover, one or more of the tasks shown and described in the context of FIG. 9 could be omitted from a practical embodiment of the insertion site recommendation process 900 as long as the intended overall functionality remains intact.

In exemplary embodiments, the insertion site recommendation process 900 is performed in connection with a patient utilizing a client application 308 to perform a new insertion. That said, in other embodiments, the insertion site recommendation process 900 may be initiated automatically in response to detecting an insertion site loss condition or in response to detecting a site rotation condition.

The insertion site recommendation process 900 identifies the particular type of medical device or insertable element to be inserted and then identifies or otherwise determines the potential insertion site locations available for the identified device (task 902, 904). For example, a CGM device or other glucose sensing arrangement may be utilized with insertion site locations in the upper arm, the abdomen, the lower back, and the upper leg, while an infusion set or infusion device may only be utilized with insertion site locations in the abdomen, the lower back, and the upper leg and an injection device may only be utilized with insertion site locations in the abdomen and the upper leg. In this regard, based on the type of device selected by the patient via the GUI display 500 and GUI elements 504, 506, 508, the client application 308 may identify an initial set of potential insertion site locations by excluding insertion site locations that are inapplicable for the selected device type. Additionally, in some embodiments, the client application 308 may filter or otherwise exclude, from the initial set of potential insertion site locations, any insertion site locations that are currently in use in connection with another device. The client application 308 may also filter or otherwise exclude potential insertion site locations that have been previously used by the patient within a threshold period of time, or insertion site locations have otherwise not been allowed to heal for more than the threshold period of time. For example, the patient may specify or otherwise configure a waiting period to be utilized by the client application 308 before recommending or indicating potential reuse of a previously used site location.

After identifying the subset of potentially available insertion site locations, the insertion site recommendation process 900 retrieves or otherwise obtains the models associated with the insertion site locations for the device type to be inserted (task 906). In this regard, for each potential insertion site, the client application 308 and/or the remote device 314 may obtain the performance models, health models, glucose forecasting models, and/or other models derived for that potential insertion site for the identified device type as described above (e.g., task 412) in the context of the insertion site modeling process 400 of FIG. 4. For each potential insertion site, the insertion site recommendation process 900 utilizes the models associated with the insertion site to calculate or otherwise determine metrics indicative of the probable performance or health of the insertion site (task 908). For example, based on the patient's current (or recent) glucose measurement data, current (or recent) insulin delivery data, current (or recent) event log data, and the duration of time since a respective insertion site was last used, and potentially other data characterizing the current state of the patient, the client application 308 may calculate or otherwise determine forecasted glucose values for the respective insertion site, a probable time in range for the respective insertion site, a probable basal insulin delivery rate for the respective insertion site, a probability of site loss for the respective insertion site, and/or the like.

After determining model-predicted metrics for each potential insertion site location, the insertion site recommendation process 900 continues by classifying or otherwise categorizing the potential insertion site locations based on their performance metrics (task 910). For example, a potential insertion site location having a predicted time in range above a threshold value and a probability of site loss below a threshold value may be classified into a high viability category, that is, a most viable group of insertion site locations which are preferred or otherwise recommended for use. Conversely, when the predicted time in range is below a threshold value or the probability of site loss is above a threshold value, the potential insertion site location may be classified into an intermediate viability category, while insertion site locations having both a predicted time in range below a threshold value and a probability of site loss above a threshold value may be classified into a low viability category or otherwise indicated as unavailable. In some embodiments, the insertion site locations may be automatically classified into different categories based on the duration of time that has elapsed since the last use independent of the model-predicted metrics. For example, any insertion site location used within the preceding week may be automatically classified into the low viability category, and any insertion site location used between 7 and 14 days ago may be automatically classified into the intermediate viability category. In this regard, there are numerous different ways different performance and usage metrics associated with potential insertion site locations may be utilized to classify insertion site locations into any number of different categories, and the subject matter described herein is not intended to be limited to any particular implementation.

In one or more embodiments, after classifying the potential insertion site locations into different viability categories, the insertion site recommendation process 900 identifies or otherwise determines one or more recommended insertion site locations (task 912). For example, in some embodiments, the client application 308 may calculate or otherwise determine a viability score for each potential insertion site as a function of the various model-predicted metrics for the insertion site and identify the insertion site location having the highest viability score as recommended. In other embodiments, the client application 308 utilize the forecasted glucose values for the potential insertion site locations to identify the insertion site location that results in predicted or forecasted glucose values over the duration of the expected lifetime of the insertion site that deviate the least from a target glucose value for the patient (e.g., using a cost function or another optimization technique). In this regard, there are numerous different ways to identify an optimal potential insertion site location as a function of the different performance, usage metrics and glucose forecasts, and the subject matter described herein is not intended to be limited to any particular implementation or recommendation algorithm.

After classifying the potential insertion site locations into different viability categories and identifying recommended insertion site locations, the insertion site recommendation process 900 generates or otherwise provides graphical indicia of the recommended insertion site locations or other guidance facilitating the patient selection of the insertion site location to be utilized (task 914). For example, as described above in the context of FIGS. 6-7, the client application 308 renders overlays for the regions of the body containing the recommended insertion site location(s) or having higher numbers of high viability insertion site locations using green or another visually distinguishable characteristic to indicate preference relative to other regions of the body having fewer high viability insertion site locations, as depicted in FIG. 6. When a region of the body is selected, the client application 308 renders the different insertion site locations within the selected region using colors or visually distinguishable characteristics to indicate the different viability states assigned to the different insertion site locations, as depicted in FIG. 7. Additionally, when one or more insertion site locations is identified as recommended, the client application 308 may highlight, emphasize, or otherwise visually differentiate the recommended insertion site location from the other depicted insertion site locations to encourage the patient to utilize the particular insertion site location. In some embodiments, the client application 308 may also generate or otherwise provide graphical representations of the model-predicted metrics associated with the displayed insertion site locations or otherwise provide explanatory information pertaining to the viability state of the displayed insertion site locations (e.g., when the patient selects or hovers over a displayed insertion site location). Thus, the patient may better understand why certain insertion site locations are recommended or discouraged, and thereby manage his or her insertion sites as desired.

In some embodiments, the patient utilizes client application 308 to create a map of potential insertion site locations on the patient's body by taking one or more images of the patient's body and entering personal information (e.g., weight, height, and the like) that allows the client application 308 to automatically identify or otherwise define the different potential insertion site locations on the different regions of the patient's body (e.g., the number, spacing, and/or density of insertion site locations). The automatically defined insertion site locations are then depicted on the insertion site selection GUI displays and utilized to associate passively-collected patient data with the corresponding insertion site location being used concurrently, as described above.

By virtue of the subject matter described herein, patients are assisted in choosing more optimal insertion site locations while avoiding insertion sites that have previously performed poorly or may be prone to overuse. The subject matter described herein may also be implemented in connection with other algorithms to detect insertion site loss conditions or insertion site rotation conditions, thereby allowing a more flexible replacement schedule to be utilized rather than replacing or rotating insertion sites preemptively. Insertion site recommendations and notifications may reduce or eliminate the need for patients to monitor or track the lifetime associated with the current insertion site, while also avoiding overuse of insertion sites and recommending insertion sites likely to perform well, thereby reducing the burden on patients and improving the user experience and patient outcome.

For the sake of brevity, conventional techniques related to glucose sensing and/or monitoring, closed-loop glucose control, sensor calibration, electrical signals and related processing, user interfaces, alerting, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be configurable to be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method comprising:
   obtaining, by a client device, historical usage data characterizing a duration and frequency with which each site location of a plurality of potential site locations on a body of a patient is used as a site for a medical device, at least some of the site locations having been used more than once;
   obtaining, by the client device, historical operational data for each site location, wherein the historical operational data comprises (a) physiological measurements performed while the medical device is operating at the site location, (b) data characterizing medicament deliveries made using the medical device, or both (a) and (b);
   obtaining a plurality of models, the plurality of models comprising a separate model generated for each site location based on relationships between a portion of the historical usage data corresponding to the respective site location and a portion of the historical operational data corresponding to the respective site location, wherein each model is executable by the client device or a remote device communicatively coupled to the client device to output a model-predicted metric that quantifies a viability of the respective site location;
   determining, using a most recent set of usage and operational data as input to the plurality of models, a current value of the model-predicted metric for each site location;
   providing, through a user interface of the client device, graphical indicia of one or more site locations that are classified as being viable based on the current value of the model-predicted metric, wherein the graphical indicia visually distinguish the one or more site locations from other site locations that are classified as being non-viable;
   updating, by the client device, the historical usage data and the historical operational data after the medical device has been applied to a first site location indicated by the graphical indicia;
   obtaining, by the client device, an updated model for the first site location, wherein the updated model is based on the updated historical usage data and the updated historical operational data;
   identifying one or more viable site locations using the updated model; and
   providing, through the user interface of the client device, graphical indicia of the one or more viable site locations identified using the updated model.

2. The method of claim 1, further comprising:
   providing, at the client device, a first graphical user interface (GUI) display including a GUI element for receiving indicia of a device type associated with the medical device;

receiving user input indicative of the device type associated with the medical device via the GUI element; and identifying the plurality of potential site locations based on the device type.

3. The method of claim 2, further comprising providing, at the client device, a second GUI display including a graphical representation of a body, wherein providing the graphical indicia of the one or more site locations comprises rendering one or more graphical overlays overlying one or more regions of the body including the one or more site locations.

4. The method of claim 3, further comprising:

in response to selection of a region of the one or more regions, providing, at the client device, a third GUI display including a graphical overlay indicating viability of a respective site location of the one or more site locations, the graphical overlay overlying a graphical representation of the selected region.

5. The method of claim 1, wherein for each site location of the plurality of potential site locations, the model-predicted metric comprises a metric indicative of a health or performance of the respective site location based on the relationships between the portion of the historical usage data corresponding to the respective site location and the portion of the historical operational data corresponding to the respective site location, and wherein the method further comprises:

identifying a current patient state based on the most recent set of usage and operational data;

calculating, for each site location of the plurality of potential site locations, a respective current value for the model-predicted metric based at least in part on the current patient state using the model for the respective site location; and classifying the one or more site locations into a viable group based on the respective current values for the model-predicted associated with the one or more site locations.

6. The method of claim 5, wherein the current patient state comprises at least one of glucose measurement data, insulin delivery data, and event log data for the patient.

7. The method of claim 1, wherein providing the graphical indicia comprises providing one or more graphical overlays corresponding to the one or more site locations overlying a graphical representation of a body.

8. The method of claim 1, wherein:

the plurality of models comprises a set of site health models;

determining the current value of the model-predicted metric comprises determining a health metric value for each site location using a site health model associated with the respective site location; and the method further comprises classifying the one or more site locations into a high viability category based on the respective health metric values.

9. The method of claim 1, wherein:

the plurality of models comprises a set of site performance models;

determining the current value of the model-predicted metric comprises determining a performance metric value for each site location using a site performance model associated with the respective site location; and the method further comprises classifying the one or more site locations into a high viability category based on the respective performance metric values.

10. The method of claim 1, further comprising:

receiving, over a network, a current measurement value for a physiological condition of the patient;

determining, for each of the one or more site locations classified as being viable, a respective forecast for the physiological condition based at least in part on the current measurement value and a respective location of the respective site location;

determining a recommended site location from among the one or more site locations classified as being viable based on the respective forecasts for the physiological condition; and providing, at the client device, a graphical indication of the recommended site location.

11. The method of claim 1, further comprising providing, at the user interface of the client device, a graphical user interface (GUI) display including one or more GUI elements for receiving user feedback regarding a performance of each site location, wherein each model is generated based on correlations between (i) the portion of the historical usage data corresponding to the respective site location, (ii) the portion of the historical operational data corresponding to the respective site location, and (iii) the user feedback for the respective site location.

12. A tangible non-transitory computer-readable medium having computer-executable instructions stored thereon that, when executed by a processor, cause the processor to:

obtain historical usage data characterizing a duration and frequency with which each site location of a plurality of potential site locations on a body of a patient is used as a site for a medical device, at least some of the site locations having been used more than once;

obtain historical operational data for each site location, wherein the historical operational data comprises (a) physiological measurements performed while the medical device is operating at the site location, (b) data characterizing medicament deliveries made using the medical device, or both (a) and (b);

provide a first graphical user interface (GUI) display at a user interface of a client device, wherein the first GUI display includes a GUI element for receiving input indicating a device type of the medical device;

identify the plurality of potential site locations based on the device type as indicated using the GUI element;

obtain a plurality of models, the plurality of models comprising a separate model generated for each site location based on relationships between a portion of the historical usage data corresponding to the respective site location and a portion of the historical operational data corresponding to the respective site location, wherein each model is executable to output a model-predicted metric that quantifies a viability of the respective site location;

determine, using a most recent set of usage and operational data as input to the plurality of models, a current value of the model-predicted metric for each site location; and provide a second GUI display at the user interface of the client device, wherein the second GUI display comprises graphical indicia overlaid on a graphical representation of the body of the patient, wherein the graphical indicia indicate one or more site locations that are classified as being viable based on the current value of the model-predicted metric, wherein the graphical indicia visually distinguish the one or more site locations from other site locations that are classified as being non-viable;

update the historical usage data and the historical operational data after the medical device has been applied to a first site location indicated by the graphical indicia;
obtain an updated model for the first site location, wherein the updated model is based on the updated historical usage data and the updated historical operational data;
identify one or more viable site locations using the updated model; and
provide, through the user interface of the client device, graphical indicia of the one or more viable site locations identified using the updated model.

13. The tangible non-transitory computer-readable medium of claim 12, wherein the computer-executable instructions cause the processor to provide a third GUI display including one or more GUI elements for receiving user feedback pertaining to performance of the plurality of potential site locations, wherein the classifications of the plurality of potential site locations are influenced by the user feedback.

14. The tangible non-transitory computer-readable medium of claim 12, wherein the computer-executable instructions cause the processor to provide a third GUI display including one or more GUI elements for receiving user feedback regarding a performance of the first site location, wherein the updated model for the first site location is further based on the user feedback regarding the performance of the first site location.

15. The tangible non-transitory computer-readable medium of claim 12, wherein the graphical indicia comprise color-coded graphical representations of the plurality of potential site locations overlying the graphical representation of the body, each site location being assigned a color representing a corresponding degree of viability.

16. The tangible non-transitory computer-readable medium of claim 12, wherein the graphical indicia comprise an indication of site location loss with respect to one or more of the plurality of potential site locations.

17. A system comprising:
a client device configured to:
obtain historical usage data characterizing a duration and frequency with which each site location of a plurality of potential site locations on a body of a patient is used as a site for a medical device, at least some of site locations having been used more than once; and
obtain historical operational data for each site location, wherein the historical operational data comprises (a) physiological measurements performed while the medical device is operating at the site location, (b) data characterizing medicament deliveries made using the medical device, or both (a) and (b);
a database configured to store the historical usage data and the historical operational data; and
a remote device communicatively coupled to the client device and the database, wherein the remote device is configured to generate a plurality of models, the plurality of models comprising a separate model generated for each site location based on relationships between a portion of the historical usage data corresponding to the respective site location and a portion of the historical operational data corresponding to the respective site location, wherein:
each model is executable to output a model-predicted metric that quantifies a viability of the respective site location;
the client device or the remote device is configured to determine, using a most recent set of usage and operational data as input to the plurality of models, a current value of the model-predicted metric for each site location; and
the client device is further configured to:
provide, through a user interface, graphical indicia of one or more site locations that are classified as being viable based on the current value of the model-predicted metric, the graphical indicia visually distinguishing the one or more site locations from other site locations that are classified as being non-viable;
update the historical usage data and the historical operational data after the medical device has been applied to a first site location indicated by the graphical indicia; and
provide, through the user interface, graphical indicia of one or more viable site locations that are identified using an updated model for the first site location, the updated model being based on the updated historical usage data and the updated historical operational data.

18. The system of claim 17, further comprising a sensing arrangement communicatively coupled to the client device, wherein:
the sensing arrangement is configured to obtain measurement data for a physiological condition of the patient, and
the client device is further configured to receive the measurement data from the sensing arrangement as part of the most recent set of usage and operational data for input to the plurality of models.

19. The system of claim 18, wherein the model-predicted metric comprises an estimated time in range for the physiological condition of the patient.

* * * * *